United States Patent [19]

Beard, Jr.

[11] Patent Number: 5,536,891

[45] Date of Patent: Jul. 16, 1996

[54] PURIFICATION OF 1,1,1,-TRICHLOROETHANE

[75] Inventor: William Q. Beard, Jr., Wichita, Kans.

[73] Assignee: Vulcan Materials Company, Wichita, Kans.

[21] Appl. No.: 255,931

[22] Filed: Jun. 7, 1994

[51] Int. Cl.$^6$ .................................................. C07C 17/38
[52] U.S. Cl. ............................................................. 570/262
[58] Field of Search ................................................ 570/262

[56] References Cited

U.S. PATENT DOCUMENTS

| | | | |
|---|---|---|---|
| 3,989,601 | 11/1976 | Boozalis et al. | 203/61 |
| 4,036,703 | 7/1977 | Leroi et al. | 203/57 |
| 4,040,990 | 8/1977 | Neely | 260/2.1 R |
| 4,267,055 | 5/1981 | Neely | 210/670 |
| 4,382,124 | 5/1983 | Meitzner et al. | 521/38 |
| 4,839,331 | 6/1989 | Maroldo et al. | 502/416 |
| 4,957,897 | 9/1990 | Maroldo et al. | 502/432 |
| 5,094,754 | 3/1992 | Maroldo et al. | 210/635 |
| 5,104,530 | 4/1992 | Maroldo et al. | 210/198.2 |

FOREIGN PATENT DOCUMENTS

| | | | |
|---|---|---|---|
| 4616801 | 5/1972 | Japan | 570/262 |

OTHER PUBLICATIONS

"Solvent Recovery by Activated Carbon Fiber," Satake et al, *Industrial Organics*, vol. 109, (1988), p. 101, Abstract No. 95073g.

*Technical Notes—Ambersorb® Carbonaceous Adsorbents: Specialty Purifications*, Rohm and Haas Co., Phiadelphia, Aug. 1990, pp. 1–11.

Specialty purifications—Ambersorb® Carbonaceous Adsorbents Liquid Phase Column Procedures, Rohm and Haas Co., Philadelphia, Oct. 1990, pp.1–6.

"THM Reductions with Ambersorb® 563 Adsorbent," Vandiver et al, Society of Soft Drink Technologists, 41st Annual Conference, Apr. 19, 1994, Albuquerque, NM, pp. 1–13.

"The Removal of Regulated Compounds From Groundwater and Wastewater Using Ambersorb® 563 Carbonaceous Adsorbent," Isacoff et al, American Institute of Chemical Engineers Annual Conference, Nov. 3, 1992, Miami Beach, Florida.

"Comparison of Ambersorb® 563 Carbonaceous Adsorbent and Granular Activated Carbon for the Removal of TCE from Water at Short Empty Bed Contact Times," Parker, Jr., American Institute of Chemical Engineers Annual Conference, Nov. 4, 1992, Miami Beach, Florida.

"Groundwater Remediation Using Ambersorb® Adsorbents," Parker, Jr., et al, The Florida Environmental Chemistry Conference, Oct. 30–Nov. 1, 1991, pp. 1–19.

*Primary Examiner*—Alan Siegel
*Attorney, Agent, or Firm*—Burns, Doane, Swecker & Mathis

[57] ABSTRACT

A process for the purification of 1,1,1-trichloroethane contaminated with at least one undesirable $C_1$–$C_3$ chlorocarbon, for example, 1,2-dichloroethane, 1,2-dichloroethylene and/or trichloroethylene, which process comprises contacting the impure 1,1,1-trichloroethane with a particulate adsorbent, the adsorbent being a particulate product of controlled pyrolysis of a polysulfonated macroporous crosslinked vinylaromatic polymer having a surface area of at least about 500 m$^2$/g, a micropore pore volume of at least about 0.24 ml/g, a macropore pore volume of less than about 0.24 ml/g and a ratio of macropore to micropore pore volume of less than 100 percent is provided.

22 Claims, 5 Drawing Sheets

PURIFICATION OF 1,1,1,-TRICHLOROETHANE

BACKGROUND OF THE INVENTION

1. Field of the Invention

This invention relates to purification of 1,1,1-trichloroethane that is contaminated with at least one undesirable $C_1$–$C_3$ chlorocarbon, for example, 1,1-dichloroethane, 1,2-dichloroethane, cis-1,2-dichloroethylene or trichloroethylene. In particular, it relates to a process for the purification of 1,1,1-trichloroethane by contacting the impure 1,1,1-trichloroethane with a special adsorbent, the adsorbent being a particulate product of controlled pyrolysis of a polysulfonated macroporous crosslinked vinylaromatic polymer having a surface area of at least about 500 $m^2/g$, a micropore pore volume of at least about 0.24 ml/g, a macropore pore volume: of less than about 0.24 ml/g and a ratio of macropore to micropore pore volume of less than 100 percent.

2. Background of the Invention

Because 1,1,1-trichloroethane is usually produced by chlorination of ethane or ethyl chloride, the product is usually contaminated with undesirable $C_1$–$C_3$ chlorocarbons such as 1,2-dichloroethane and trichloroethylene, which detract from the usefulness of the 1,1,1-trichloroethane produced. While various methods for the purification of 1,1,1-trichloroethane have been attempted, such methods have achieved only moderate success. For example, while removal of relatively large quantities of 1,2-dichloroethane has been accomplished by extractive distillation, the 1,2-dichloroethane levels in the 1,1,1-trichoroethane are reduced only to around 0.05 percent. Examples of such processes have been demonstrated by Leroi et al, *Ger. Offen.* DE 2,627,992 (20 Jan. 1977), by Boozalis et al, U.S. Pat. No. 3,989,601 (2 Nov. 1976) and by Gabler et al, *Ger. Offen.* DE 2,036,939 (3 Feb. 1972). Trichloroethylene is usually removed by ordinary distillation processes, but small residues remain unless a highly efficient distillation column is used. A further problem of various prior art processes is that decomposition of the 1,1,1-trichloroethane often results because of the heat applied or because of chemical reaction.

A number of these various prior processes for the purification of 1,1,1-trichloroethane are sufficient for many purposes, e.g., when the solvent is intended for use in degreasing. Such processes of purification, however, are inadequate for certain applications which require the use of 1,1,1-trichloroethane of very high purity. For example, when 1,1,1-trichloroethane is used as an intermediate for the synthesis of fluorohydrocarbons and chlorofluorohydrocarbons, much lower levels of both 1,2-dichloroethane and trichloroethylene are desired.

The present invention provides a process capable of reducing the levels of 1,1-dichloroethane, 1,2-dichloroethane, dichloroethylene and trichloroethylene to less than about 10 ppm, and even to less than about 1 ppm, without decomposition of 1,1,1-trichloroethane.

Various forms of activated carbon have been used to remove certain chlorocarbons and their mixtures from aqueous solutions, but not for the separation of the chlorocarbons from each other. An example of the use of carbon fibers for the recovery, but not separation, of various chlorocarbon solvents is disclosed in Satake, et al, *Kagaku Sochi*, 30(3), 93–7 (Japan) 1988 (Chem. Abs. 109:95073 g).

In view of the limited success of prior art purification processes for 1,1,1-trichloroethane, there thus exists a long felt need in the art for a process for the purification of 1,1,1-trichloroethane which will reduce the concentration of undesirable chlorocarbons to an art-accepted level without decomposition of the desired product. There is also a need in the art for a purification process that is capable of separating the removed chlorocarbons from each other.

SUMMARY OF THE INVENTION

The present invention provides a process for the purification of 1,1,1-trichloroethane which is contaminated with at least one undesirable $C_1$–$C_3$ chlorocarbon. This process comprises contacting the impure 1,1,1-trichloroethane with a particulate adsorbent in an adsorption zone for a time at least sufficient to reduce the concentration of undesirable chlorocarbon to a level acceptable in the art, e.g., to less than 100 ppm, or even to less than 1 ppm. The reduced concentration of undesirable chlorocarbons obtained will depend on the concentration of impurities in the 1,1,1-trichloroethane to be purified and the intensity of treatment applied. The adsorbent used in the process is a particulate product of controlled pyrolysis of a polysulfonated macroporous crosslinked vinylaromatic polymer having a surface area of at least about 500 $m^2/g$, a micropore pore volume of at least about 0.24 ml/g, a macropore pore volume of less than about 0.24 ml/g and a ratio of macropore to micropore pore volume of less than about 100 percent.

In a preferred embodiment, the adsorbent has a surface area of between about 500 and 1100 $m^2/g$, a micropore pore volume of between about 0.24 and about 0.41 ml/g, a macropore pore volume of between about 0.14 and about 0.23 ml/g, and a ratio of macropore to micropore pore volume of between about 50 and about 90 percent. For instance, one preferred adsorbent which is commercially available has a surface area of about 500 to about 600 $m^2/g$, most preferably about 550 $m^2/g$, a micropore pore volume of about 0.24 ml/g, a macropore pore volume of about 0.14 ml/g, and a ratio of macropore to micropore pore volume of about 58 percent. Another very desirable, commercially available adsorbent has a surface area of from about 750 to about 850 $m^2/g$, most preferably about 800 $m^2/g$, a micropore pore volume of about 0.32 ml/g, a macropore pore volume of about 0.20 ml/g, and a ratio of macropore to micropore pore volume of about 63 percent.

The undesirable $C_1$–$C_3$ chlorocarbons which may be removed from the 1,1,1-trichloroethane by the present invention include, for example, 1,2-dichloroethane, 1,1-dichloroethane, cis-1,2-dichloroethylene, trichloroethylene and the like. Although higher concentrations are possible, the 1,1,1-trichloroethane to be purified will generally comprise up to about 10,000 ppm, and more particularly between about 10 and about 10,000 ppm, of 1,2-dichloroethane, 1,1-dichloroethane, cis-1,2-dichloroethylene, trichloroethylene or a mixture thereof. The temperature at which the process is conducted will preferably be between about 0° and about 50° C., and may be room temperature. The process of the present invention is capable of reducing the concentration of undesirable chlorocarbon in the 1,1,1-trichloroethane to between about 1 and about 100 ppm, preferably to between about 1 and about 50 ppm. In many instances, concentration of undesirable chlorocarbons in the 1,1,1-trichloroethane may be reduced to less than 1 ppm. Subsequently, the adsorbed chlorocarbons may be stripped and regenerated from the adsorbent in ways that are otherwise known.

For example, the chlorocarbons may be removed from the particulate adsorbent by stripping with steam or with an inert gas such as nitrogen, carbon dioxide, argon, methane, or ethane, by heat alone, or by combination of stripping gas and heat. Alternatively, the chlorocarbons may be regenerated from the particulate adsorbent by elution with a liquid eluent, such as methylene chloride, methanol, acetone, or hot methylchloroform.

Finally, the present invention relates to a process for selectively removing at least one undesirable $C_1$–$C_3$ chlorocarbon, using the above identified adsorbents, in a concentration generally no greater than about 10,000 ppm, e.g., between about 1 and about 10,000 ppm from 1,1,1-trichloroethane. This process comprises contacting the impure 1,1,1-trichloroethane with a particulate adsorbent at a temperature between about 0° and about 50° C. for a time at least sufficient to remove the undesirable chlorocarbon to a concentration of at most about 100 ppm, more preferably between about 1 and about 50 ppm and even to a concentration of less than about 1 ppm. The $C_1$–$C_3$ chlorocarbon can then be regenerated by selecting an appropriate regeneration process for the $C_1$–$C_3$ chlorocarbons. If more than one $C_1$–$C_3$ chlorocarbon is removed they can be separately regenerated by selecting the appropriate regeneration process.

DESCRIPTION OF THE PREFERRED EMBODIMENTS OF THE INVENTION

It has been found that 1,1,1-trichloroethane comprising as an impurity at least one other $C_1$ to $C_3$ chlorocarbon, and in particular 1,2-dichloroethane and/or trichloroethylene, can be effectively purified by contacting the impure 1,1,1-trichloroethane with a special particulate adsorbent. It has also been found that such purification avoids or minimizes decomposition of 1,1,1-trichloroethane.

The special adsorbents used in the present invention are well known per se and are particulate products obtained in a known manner by controlled pyrolysis of polysulfonated macroporous crosslinked vinylaromatic polymers. The special adsorbent particles of this kind which are useful for the present invention are required to have a surface area of at least about 500 m²/g, a macropore pore volume of less than about 0.24 ml/g and a ratio of macropore to micropore pore volume of less than about 100 percent. Suitable products are commercially available, for instance, from Rolhm and Haas Company under its "Ambersorb" trademark. For instance, certain carbonaceous adsorbents produced by Rohm and Haas Company's Supelco Division and sold under the tradename "Ambersorb"™ 563, 564, 572, and 575 have the required properties and may thus be used in the process of the invention. These adsorbents are described in U.S. Pat. Nos. 4,839,331; 4,957,897; 5,094,754; and 5,104,530, all to Maroldo et al and assigned to Rohm and Haas Company, which description is hereby incorporated by reference in its entirety. Typical properties for the family of these various "Ambersorb"™ adsorbents are as follows:

| Property | Ambersorb ™ 563 | Ambersorb ™ 564 | Ambersorb ™ 572 | Ambersorb ™ 575 |
|---|---|---|---|---|
| Hydrophobicity Ranking | 1[1] | 2 | 4 | 3 |
| Particle Size (Mesh) | 20/50 | 20/50 | 20/50 | 20/50 |
| Surface Area (m²/g)[2] | 550 | 550 | 1100 | 800 |
| Density (g/cc) | 0.53 | 0.60 | 0.49 | 0.55 |
| Microporosity (ml/g)[3] | 0.23 | 0.24 | 0.41 | 0.32 |
| Mesoporosity (ml/g)[3] | 0.14 | 0.13 | 0.19 | 0.20 |
| Macroporosity (ml/g)[3] | 0.23 | 0.14 | 0.24 | 0.20 |
| Ratio of Macro/Microporosity (%) | 100 | 58.3 | 58.5 | 62.5 |

[1] Most Hydrophobic
[2] BET Surface Area, Single Point Micromeritics 2300
[3] Nitrogen Porosimetry, Micromeritics 2400

More specifically, these adsorbent particles are macroporous particles prepared by partial pyrolysis of macroporous polysulfonated polymers in an otherwise known manner. As used herein, macroporous copolymers include macroporous or macroreticular copolymers prepared by suspension polymerization in the presence of a precipitant, as described in U.S. Pat. No. 4,256,840 and U.S. Pat. No. 4,224,415, and copolymers into which large pores have been introduced by other methods as, for example, the technique described in U.S. Pat. No. 3,122,514.

The vinyl aromatic polymers useful in making suitable adsorbents are those in which at least 50% of the crosslinked monomeric units contain a vinylaromatic group. Preferred are vinylaromatic polymers in which at least 90% of the crosslinked monomeric units contain a vinylaromatic group. Especially preferred are vinylaromatic polymers where at least 98% of the crosslinked monomeric units contain a vinylaromatic group. Vinylaromatic monomers include, among others, styrene, alpha-methylstyrene, vinyltoluene, p-methylstyrene, ethyl-vinylbenzene, vinylnaphthalene, divinylbenzene, trivinylbenzene, vinylisopropenylbenzene, diisopropenylbenzene, and the like. Especially preferred are styrene, divinylbenzene (which will normally contain some ethylvinylbenzene), and diisopropenylbenzene.

Polysulfonation, as used herein, refers to a sulfonation process that is sufficiently vigorous to introduce an average of more than one sulfonate group, e.g., between about 1.04 and about 1.16 sulfonate groups, per accessible aromatic nucleus. Such vigorous sulfonation is accompanied by the formation of a significant number of sulfone crosslinks, in which sulfonate groups bridge between two aromatic nuclei to form —$SO_2$— crosslinks.

As the polysulfonation produces both sulfonate and sulfone groups, analytical identification of the polysulfonated adsorbent is best done by conventional microanalytical procedures for elemental sulfur content. A polysulfonated adsorbent, as used herein, is thus one in which sulfur is introduced into the adsorbent molecular structure by the above sulfonation process. In general, conventional sulfuric acid sulfonation of lightly crosslinked copolymers will introduce approximately the same amount of sulfur as would theoretically be expected for complete monosulfonation of the copolymer. In highly crosslinked copolymers, however, sulfonation tends to occur predominantly at or near the surface of the copolymer particle, and to a lesser extent at increasing distances from the surface. Polysulfonation exhibits a similar phenomenon; a highly crosslinked, polysulfonated copolymer may contain less sulfur than theoretically expected for monosulfonation, yet the accessible aromatic nuclei will be polysulfonated.

Sulfone crosslinking occurs under the same vigorous reaction conditions required to achieve polysulfonation, and is therefore present in polysulfonated adsorbents. The preparation of such adsorbents is described, for example, in U.S. Pat. No. 3,158,583. Instead of two-step sulfonations described in the reference, the copolymers may also be polysulfonated with oleum, i.e., fuming sulfuric acid (a solution of sulfur trioxide in sulfuric acid), to obtain a polysulfonated adsorbent operable in the present invention. Other procedures for preparing polysulfonated aromatic cation exchange adsorbents will be apparent to those skilled in the art.

The preferred copolymers to be polysulfonated are macroporous copolymers prepared by copolymerizing a monovinyl aromatic monomer, preferably styrene, and a polyvinyl crosslinking monomer, preferably diisopropenylbenzene or divinylbenzene. The polyvinyl crosslinker level in the copolymer may be from about 2% to about 98% by weight of the copolymer, with the preferred range being from about 3% to about 80% by weight of the copolymer. Other suitable crosslinkers include those discussed in U.S. Pat. No. 4,040,990. Combinations of crosslinkers may also be used.

Particularly preferred are copolymer particles produced in bead form by suspension polymerization, and more particularly preferred are those in which a precipitant such as those taught in U.S. Pat. No. 4,256,840 is included in the suspension mixture to produce macroporous polymer beads. The bead form is preferred as the physical integrity of beads of pyrolyzed polymers is greater than that of other particulate (spherical) adsorbents.

As previously stated, the macroporous or macroreticular copolymers are prepared by suspension polymerization in the presence of a precipitant. Saturated higher aliphatic hydrocarbons, such as heptane, isooctane and the like, may be employed as precipitants. The precipitant may generally be present in ratios from about 20 parts per 100 parts of monomer to about 600 parts per 100 parts of monomer, depending on the crosslinking level desired and the particular precipitant used.

The pore structure of the final product must contain at least two distinct sets of pores of differing average size, i.e., a multimodal pore distribution. The pores may be classified as being macropores, micropores or mesopores. In the present text, the term "macropore" is used to mean pores of average diameter from about 3.5 nm to about 10000 nm, although values of about 3.5 nm to about 50 nm are preferred. "Micropore" refers to pore values of average diameter about 0.10 nm to about 3.5 nm, preferably about 0.15 nm to about 2 nm. A subcategory of micropores is "mesopores," which term is used herein to mean pores having an average diameter from about 0.6 nm to about 3.5 nm.

Although adsorbent beads of the size produced by conventional suspension polymerization processes are of a useful size for various further reactions and end uses, the polymerization process parameters may be purposely adjusted to produce larger or smaller beads of pyrolyzed polymers, and even ground macroporous adsorbents produced in non-bead form may be used. For example, the adsorbents may be further ground or selectively sieved to produce the desired particle size.

A preferred method for conducting the polysulfonation is to contact the macroporous adsorbent with fuming sulfuric acid, i.e., concentrated sulfuric acid containing dissolved sulfuric acid, for a period of from about 5 hours to about 20 hours or more at a temperature of from about 100° to about 150° C. Particularly preferred is treatment at about 120° C. for a period of about 16 hours. The fuming sulfuric acid may have a specific gravity of from about 1.88 to about 2.00 and is used in amounts of from about 100% to about 2000% or more, based on the weight of the macroporous adsorbent. A preferred set of conditions is to use 20% oleum, specific gravity 1.915, at from about 1400 to about 1500%. The polysulfonated adsorbent is preferably hydrated, then washed to remove acid and dried prior to calcining. As is known in the art, care must be taken in the hydration step not to shatter the adsorbent by direct contact with water; hydration with diluted sulfuric acid is preferred.

The pyrolysis may be conducted by any of the methods taught by Neely, U.S. Pat. No. 4,040,990. Preferred is a controlled pyrolysis at temperatures from about 300° to about 1200° C. for a period of about 15 minutes to about two hours. In the absence of activating chemicals, the pyrolysis may be maintained longer at the upper temperature with very little change taking place in weight loss or pore size development of the polymer. The polymer may be agitated and/or heated with steam or hot gases, or it may be heated under static conditions under nitrogen. A fluidized bed treatment may be used, in which heated nitrogen is passed upward through the bed with the gas also serving to agitate the bed particles. The polymer may be introduced directly into the oven at the highest temperature desired, or it may be heated in several steps to the final temperature.

A distinct advantage in using polysulfonated adsorbents, compared with monosulfonated adsorbents, when making the preferred adsorbents is that the polysulfonated adsorbents produce little or no tarry products (which can clog the gas exhaust line and foul the pyrolysis apparatus) during pyrolysis. Any tars that are produced will be of lower molecular weight and thus more volatile. The pyrolyzed polysulfonated adsorbents thus exhibit less weight loss than the monosulfinated adsorbents under similar pyrolysis conditions, which, therefore, results in a higher yield of useful carbonaceous material. It has been stated in the prior art that the improved evolution of gases during pyrolysis is believed to contribute to the higher pore volume caused by outgassing.

The carbonaceous material produced from the polysulfonated material may be used as such in the present invention, or it may be activated further by processes known in the art, such as exposure to various activating gases, including oxygen, steam, water, ammonia, carbon monoxide, carbon dioxide, and the like, at temperatures from about 300° to about 1200° C., or more. Activation in the presence of steam at about 800° to about 1000° C. is preferred.

It is also possible to conduct the pyrolysis in the presence of an activating gas rather than an inert gas such as nitrogen. At temperatures below about 800° C., pyrolysis is the kinetically dominating process, and little effect of the activating gas is seen at relatively short pyrolysis times. At pyrolysis temperatures above about 800° C., or with lengthy exposure to the activating gas at temperatures between about 300° and about 800° C., both pyrolysis and activation can be accomplished. Activation with reactive gases is an optional process which may be used for the modification of adsorbent properties, but is not necessary for the process of the present invention as long as the required physical characteristics of the adsorbent are achieved in any other suitable manner.

It has now been unexpectedly found that these adsorbents produced by the controlled pyrolysis of a polysulfonated macroporous crosslinked vinylaromatic polymer, and in particular the pyrolyzed polysulfonated crosslinked vinylaromatic polymer adsorbents known as "Ambersorb"™ 564 and 575, are capable of removing considerable quantities of trichloroethylene, 1,1-dichloroethane, 1,2-dichloroethane and cis-1,2-dichloroethylene from 1,1,1-trichloroethane without any observable decomposition of the 1,1,1-trichloroethane. In fact, trichloroethylene, 1,2-dichloroethane and cis-1,2-dichloroethylene can be removed from 1,1,1-trichloroethane to a level non-detectable by a flame ionization chromatograph, i.e., less than 1 ppm. The adsorption capacities of the preferred "Ambersorb"™ adsorbents using a commercial 1,1,1-trichloroethane product in the range of availability (471 ppm 1,2-dichloroethane, 223 ppm trichloroethylene and 238 ppm cis-1,2-dichloroethylene) were as high as 7.4 weight percent 1,2-dichloroethane, 3.5 weight percent trichloroethylene, and 3.7 weight percent cis-1,2-dichloroethylene. Furthermore, using these adsorbents, the level of vinylidene chloride in the effluent was less than in the starting impure 1,1,1-trichloroethane, indicating that little, if any, dehydrochlorination and some adsorption was occurring. This is in contrast to other adsorbents tested, the best of which (Zeolite 5A), under the same conditions, generally has a capacity of only about 2 to 3 weight percent 1,2-dichloroethane and about 1 weight percent trichloroethylene.

The "Ambersorb"™ adsorbents used in the process of the present invention can be repeatedly regenerated, for example, by heat stripping with steam, air or an inert gas and other regeneration methods known in the art. Thus, the adsorbents may be repeatedly used in many adsorption/regeneration cycles without noticeable loss in adsorption capability.

For a liquid phase purification of the 1,1,1-trichloroethane, the adsorbents can be used effectively in either a batch or column mode. Operation in a vertical column containing a fixed, packed bed of adsorbent is preferred, as it is more efficient. The 1,1,1-trichloroethane is preferably purified in an upflow operation to prevent the accumulation of air bubbles, but downflow may be used if desired for any reason.

The preferred system configuration will be dependent on a number of variables, including the effluent criteria, vessel design constraints, and eventual regeneration technique used. Typically, if extremely low leakage levels must be met, countercurrent regeneration is recommended. Concurrent operation is usually easier from an operational standpoint, but results in slightly higher leakage levels once the column is returned to service after regeneration.

Service flow rate will depend on various factors, including concentrations of impurities in feed stream, effluent targets, adsorptivity of compounds present, and vessel efficiency. Adsorption flow rates can vary from 0.25 gallons per minute per cubic foot of (gpm/ft$^3$) adsorbent up to 8 gallons per minute per cubic foot of adsorbent. Although column studies should be completed to determine optimum flow rate conditions, typically a flow rate of 3 to 4 gallons per minute per cubic foot of adsorbent is preferred.

A minimum bed depth of one foot is generally recommended for the column. If a possibility for buildup of particulate matter on the top of the bed exists, then the vessel should be designed to allow sufficient room for backwashing (up to 100 percent bed expansion). The buildup of particulate matter is undesirable as suspended solids and particulate matter can cause pressure drop problems, channeling in the bed and possibly foul the adsorbent. Prefiltration (deep bed filter, cartridge filter or other suitable filtration device) is recommended, especially if the column will be in service for an extended period of time.

Preliminary column tests to assess optimum flow rates and adsorbent usage to maintain effluent quality to a set breakthrough concentration are recommended as the breakthrough concentration of the column will vary depending on various factors such as influent concentrations, effluent targets, adsorptivity of compounds present and vessel efficiency. Such test procedures are generally known in the art.

The capability to easily regenerate the adsorbent bed in situ is an important feature for an adsorbent system. Regeneration of the adsorbent bed greatly improves the cost-effectiveness of the process. The proper regenerant will depend on the solubility of each adsorbate as well as the ease of handling and disposal of the concentrated contaminant or spent regenerant stream. Generally, the adsorbents of the present invention can be regenerated by stripping with steam or other inert gases and heat, or they can be eluted with a liquid eluent, such as methylene chloride, methanol or acetone.

When using steam as the regenerant for the chlorocarbon compounds, clean saturated or superheated steam at a pressure of about 5 to about 40 psig and at a temperature of about 105° to about 200° C., for example, can be passed through the bed. The stream is then condensed and sent to a phase separation vessel. The steam condensate contains a separated contaminant layer (typically less than one bed volume of contaminant). Steam flow rates (measured as condensate) of about 0.25 to about 6 bed volumes per hour (BV/hr) can be used. Optimum regeneration efficiency while minimizing cycle time can be achieved by using a lower flow rate for the initial steam introduction followed by higher flow rates during later stages. The total number of bed volumes of steam condensate can be optimized based on effluent targets and required minimum service cycle times. With respect to chlorocarbons, up to 20 bed volumes of steam as condensate are required to consistently meet more stringent effluent criteria.

After steam regeneration, the adsorbent bed should be cooled to the desired temperature with a recycle of cooled nitrogen. Alternatively, it can first be cooled to 90° C. with nitrogen and then to the desired adsorption temperature with a recycle of cooled methylchloroform, i.e., 1,1,1-trichloroethane. If particulate matter buildup is a problem, a full backwash of the adsorbent can be done to remove suspended solids.

In solvent regeneration, an appropriate solvent such as methanol, acetone or methylene chloride is passed through the bed at a flow rate of 2. Either upflow or downflow regeneration is acceptable. Typically about three or four bed volumes of regenerant can recover most of the material adsorbed. In many cases, much less regenerant can be used to achieve a complete regeneration, but this depends on the regenerant and adsorbate employed. It is, therefore, recommended that regeneration efficiency studies be completed to optimize regeneration conditions. A regenerant eluate curve (concentration of contaminant as a function of volume of regenerant used), as known in the art, may be produced to help define optimum flow rates and cycle times.

Following regeneration, a purge with water, steam or inert gas is recommended to remove any residual regenerant prior to the next adsorption cycle. An eluate curve (concentration of regenerant in water as a function of water collected), for example, may be used to determine the quantity of water required for purging. Practice with methyl chloroform indicates no necessity for purging entrapped air as long as the operation is carried out in an upflow configuration. If particulate matter buildup results, a full wash can be done to remove any suspended solids.

In order to illustrate the present invention and the advantages thereof, the following specific examples are given, it being understood that the same is intended only as illustrative and in nowise limitative.

EXAMPLES

Example 1

Screening of Potential Adsorbents for Removal of 1,2-Dichloroethane From 1,1,1-Trichloroethane Equal size samples of various potential adsorbents were weighed out into 125 ml screwcap bottles with Teflon® seals. To each was added 100 g of 1,1,1-trichloroethane (MCF) containing 400–1000 ppm of 1,2-dichloroethane (EDC) and in some cases also 500 ppm of trichloroethylene (TCE), as indicated below. Each was shaken on a mechanical shaker for 2 hours after which time a sample was withdrawn and analyzed by gas chromatography with a flame ionization detector. The results are shown in Tables I, II and III.

TABLE I

| EDC Content in MCF = 435 ppm | | | |
|---|---|---|---|
| Adsorbent sample size = 0.5 g | | | |
| Manufacturer | A | A | B |
| Designation | Activated-1 | Activated-2 | Activated |
| Material | Carbon | Carbon | Carbon |
| Form | powdered | powdered | powdered |
| Solvent analysis after shaking: | | | |
| EDC ppm | 402 | 374 | 360 |

TABLE II

| EDC Content in MCF = 471 ppm | | | | | | | |
|---|---|---|---|---|---|---|---|
| Adsorbent sample size = 5.0 g | | | | | | | |
| Manufacturer | | | | | Rohm and Haas Ambersorb ™ | | |
| Tradename | | | C | B | 564 | 572 | 575 |
| Designation | | | 5A | Activated | Carbonaceous | | |
| Material | Cellulose | Pumice | Zeolite | Carbon | Adsorbents | | |
| Form | chips | ground | extrusions | spheres | spheres | | |
| Solvent analysis after shaking: | | | | | | | |
| EDC, ppm | 502 | 479 | 30.9[a] | 147 | ND[b] | ND[b] | 16.7 |
| Vinylidene Chloride, ppm | — | — | 315 | — | 13.2 | 12.0 | 11.1 |
| TCE, ppm | — | — | 239 | — | ND[b] | ND[b] | ND[b] |

[a]Also caused MCF dehydrochlorination.
[b]Not detected, <1 ppm.

TABLE III

| EDC Content in MCF = 1000 ppm | | | | |
|---|---|---|---|---|
| TCE Content in MCF = 500 ppm | | | | |
| Adsorbent sample size = 5.0 g | | | | |
| Manufacturer | | Rohm and Haas | | |
| Tradename | | Ambersorb ™ | | |
| Designation | 563 | 564 | 572 | 575 |
| Material | | Carbonaceous Adsorbents | | |

TABLE III-continued

| Form | spheres | | | |
|---|---|---|---|---|
| Solvent analysis after shaking: | | | | |
| EDC, ppm | 66 | 7.6 | 171 | 43.8 |
| TCE, ppm | ND | ND | ND | ND |

Example 2

Continuous Adsorption of 1,2-Dichloroethane, Trichloroethylene and cis-1,2 -Dichloroethylene from 1,1,1-Trichloroethane A. A glass column drawn down to accommodate ⅜-inch plastic fittings on each end and having an internal diameter of 1.24 cm was loaded to a height of 56 cm with "Ambersorb"™ 564 carbonaceous adsorbent beads. Glass wool plugs served as retainers on each end. 1,1,1-Trichloroethane containing about 471 ppm of 1,2-dichloroethane (EDC), 223 ppm of trichloroethylene (TCE) and 238 ppm of cis-1,2-dichloroethylene (cis-DCE) was pumped in through the top of the column with a peristaltic pump equipped with "Viton"™ tubing at a rate of approximately 2.2 ml/minute. The top of the column was fitted with a tee to disengage air bubbles. Samples were taken periodically and breakthrough was determined from a curve of 1,2-dichloroethane concentration versus time. The results are shown in Table IV.

B. A second smaller glass column was constructed as above except that a glass frit was used as a retainer at the bottom. The column had an internal diameter of 1.06 cm and a usable bed length of about 10 cm. It was loaded with 5.00 g of "Ambersorb"™ 564 adsorbent, which was retained with a small glass wool plug at the top. 1,1,1-Trichloroethane containing about 471 ppm of 1,2-dichloroethane, 223 ppm of trichloroethylene and 238 ppm of cis-1,2-dichloroethylene was pumped in through the bottom of the column at two different rates and the purified 1,1,1-trichloroethane allowed to overflow into a receiver. Samples were taken periodically at the top of the column and breakthrough was determined from a curve of 1,2-dichloroethane concentration versus time. The results are shown in Table IV.

Example 3

Example 2 was repeated using a column loaded with 5.00 g of "Ambersorb"™ 575 adsorbent. The results of this example are shown in Table V.

TABLE IV

Laboratory Column Capacity Tests
with "Ambersorbs"™ 564 and 575

| Experiment No. | 1 | 2 | 3 | 4 | 5 |
|---|---|---|---|---|---|
| Adsorbent No. | 564 | 564 | 564 | 575 | 575 |
| Column Diameter, cm. | 1.25 | 1.05 | 1.05 | 1.05 | 1.05 |
| Column Length, cm. | 56 | 10 | 10 | 10 | 10 |
| Temperature, °C. | 23 | 23 | 23 | 23 | 23 |
| Residence Time, minutes | 34 | 3.8 | 1.1 | 8.2 | 8.2 |
| Space Velocity, gpm/ft$^{2a}$ | 0.40 | 0.58 | 2.02 | 0.27 | 0.27 |
| MCF Feed, ppm: | | | | | |
| EDC | 471 | 471 | 471 | 471 | 450 |
| TCE | 223 | 223 | 223 | 223 | 0 |
| cis-DCE | 238 | 238 | 238 | 238 | 0 |
| Calculated Capacities to Breakthrough$^b$, weight percent: | | | | | |
| EDC | 7.37 | 5.50 | 2.75 | 2.64 | 5.27 |
| TCE | 3.49 | 2.60 | 1.30 | 1.25 | — |
| cis-DCE | 3.72 | 2.78 | 1.39 | 1.33 | — |
| Totals | 14.58 | 10.88 | 5.44 | 5.22 | 5.27 |

$^a$Gallons per minute per square foot of cross-sectional area
$^b$First appearance of EDC in effluent, TCE and cis-DCE still non-detectable

Example 4

Adsorption and Thermal Desorption Tests

A. Adsorption—Five samples of about 5.00 g of "Ambersorb"™ 563 adsorbent were weighed to four decimal places into 125 ml bottles. Approximately 80 ml of either water, 1,1,1-trichloroethane, dichloromethane, 1,2-dichloroethane or trichloroethylene was poured individually as an adsorbate into a bottle containing the "Ambersorb"™ 563 adsorbent. Each of the bottles was then tightly sealed with PTFE-lined caps and clamped in a reciprocating shaker for two hours.

B. Thermal Desorption—The bulk of each treated adsorbate was removed from the beads with a syringe pipet, with great care being exercised not to remove even one bead. The remaining adsorbate was removed by a slow stream of air, with some heating when necessary, until the beads were no longer noticeably wet. The bottles were then placed in a circulating air oven and heated at 105° C. for 16 hours. They were then removed from the oven, cooled to room temperature with the cap just loose enough to maintain atmospheric pressure, and weighed to four decimal places. This heating, cooling and weighing procedure was then repeated at temperatures of 150° C. and 200° C.

The same procedure was conducted with "Ambersorb"™ 564, 572 and 575 adsorbents, using the same adsorbates of water, 1,1,1-trichloroethane, dichloromethane, 1,2-dichloroethane and trichloroethylene.

Figure 1:
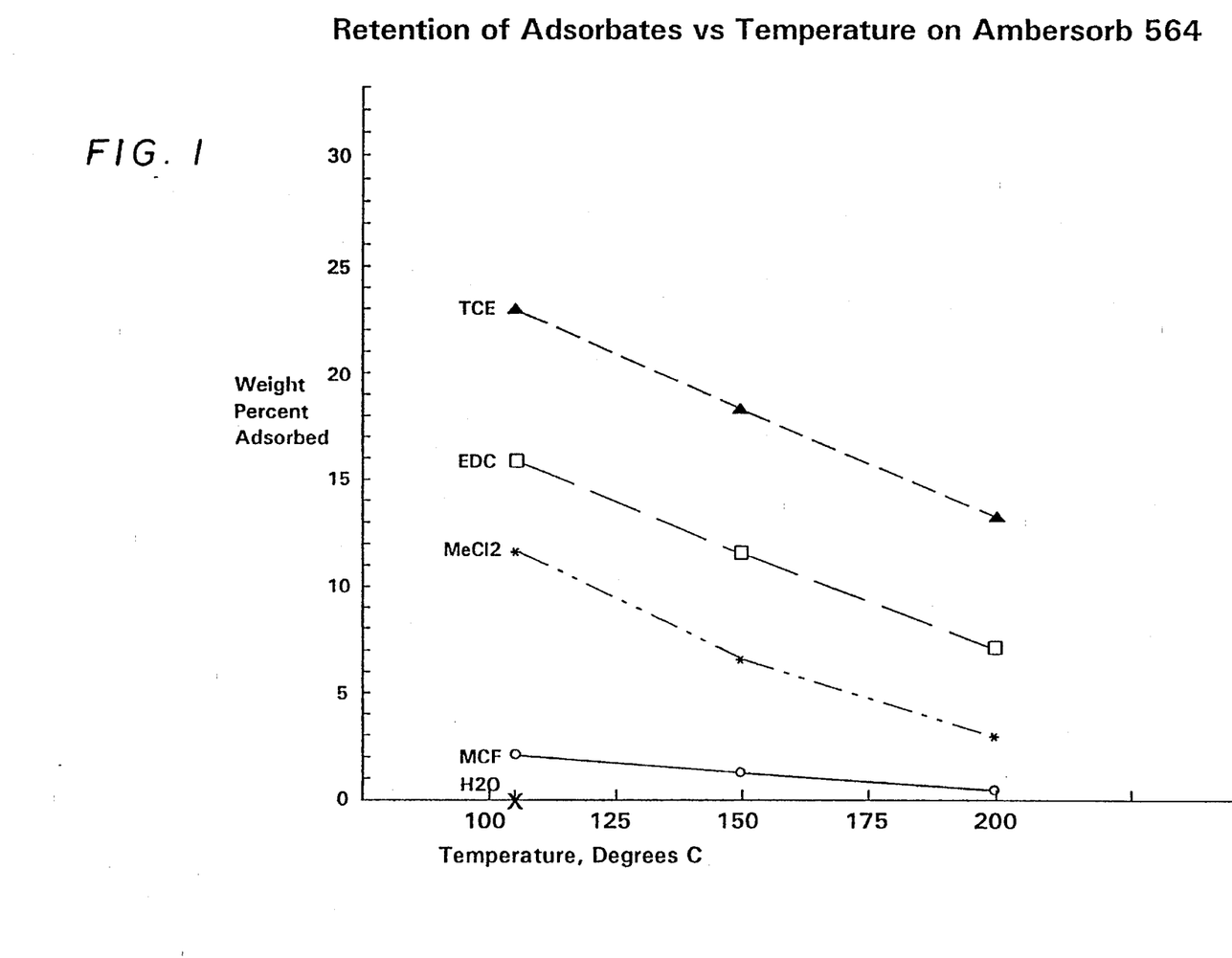
FIGS. 1–4 illustrate thermal desorption curves which plot adsorbate retentions of 1,1,1-trichloroethane, dichloromethane, 1,2-dichloroethane and trichloroethylene in weight percent against temperature.
Figure 2:
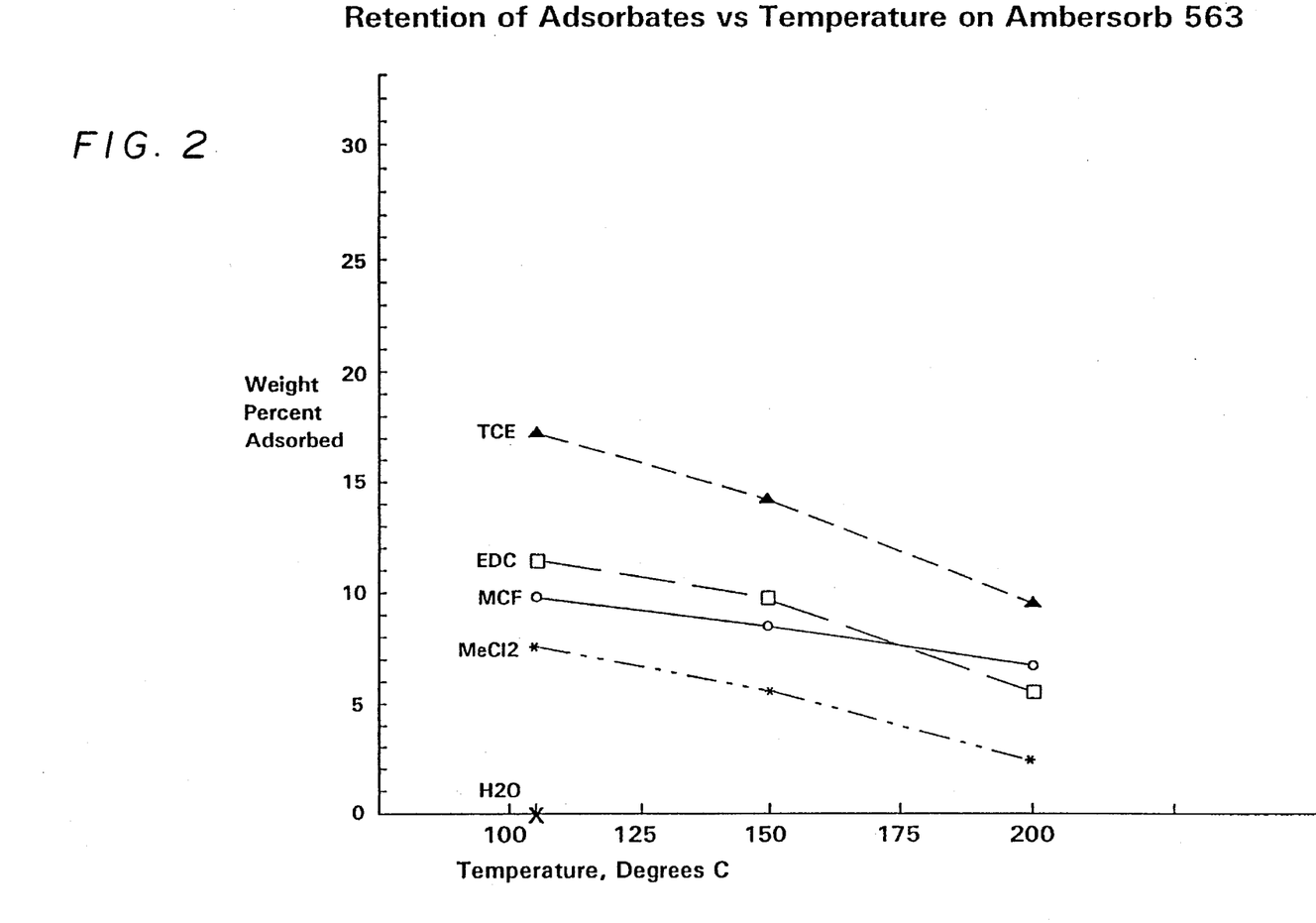
Figure 3:
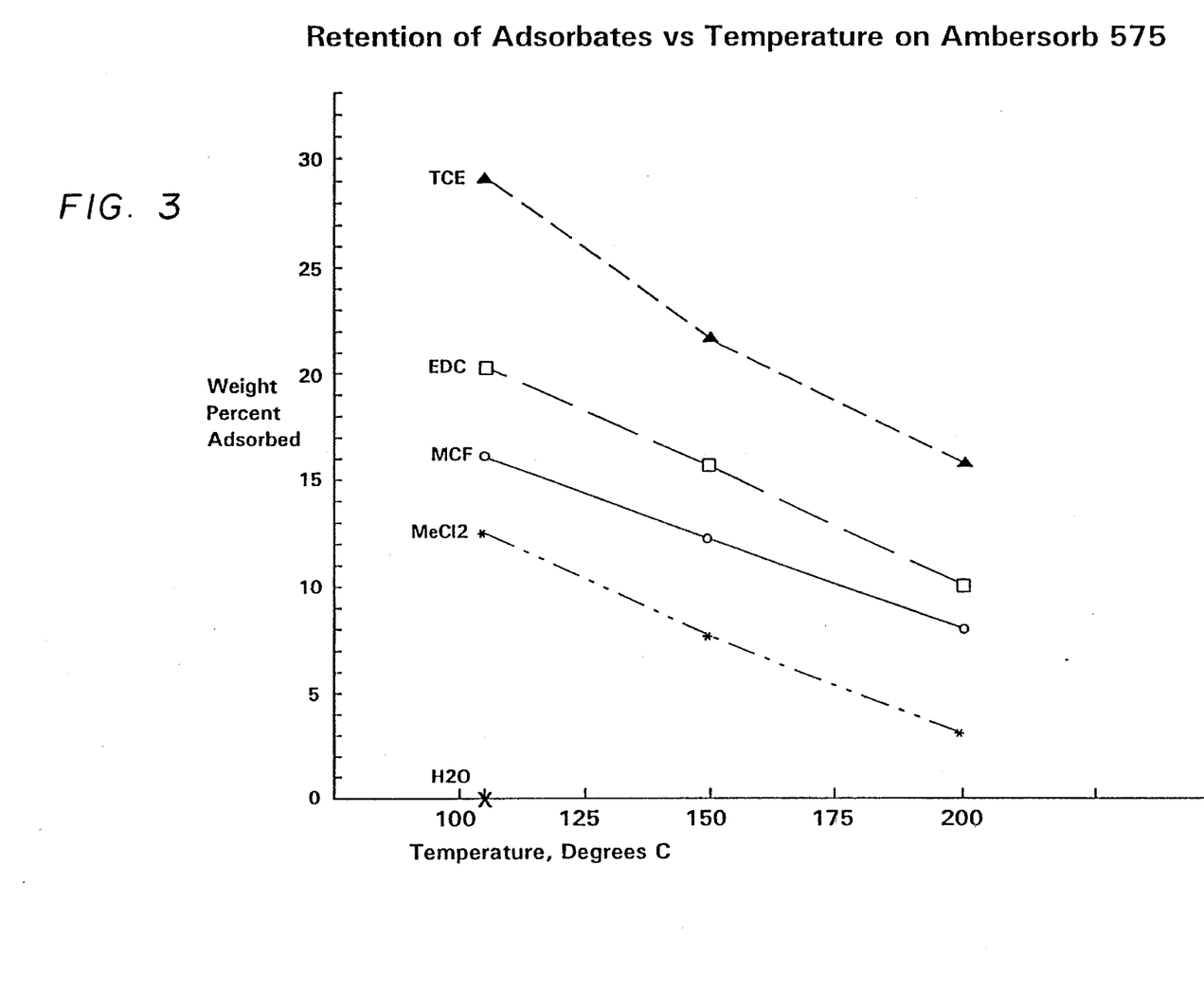
Figure 4:
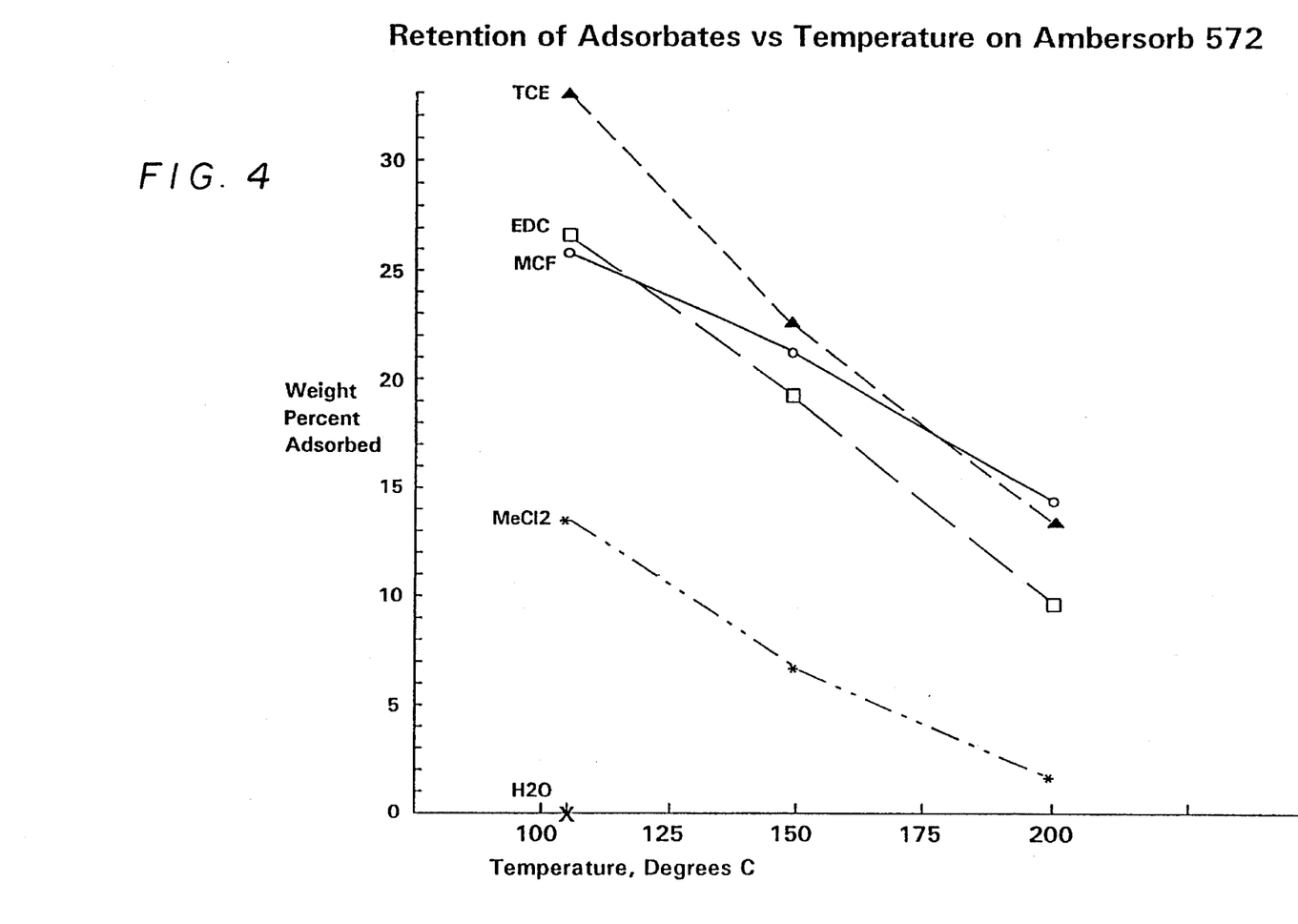
Figure 5:
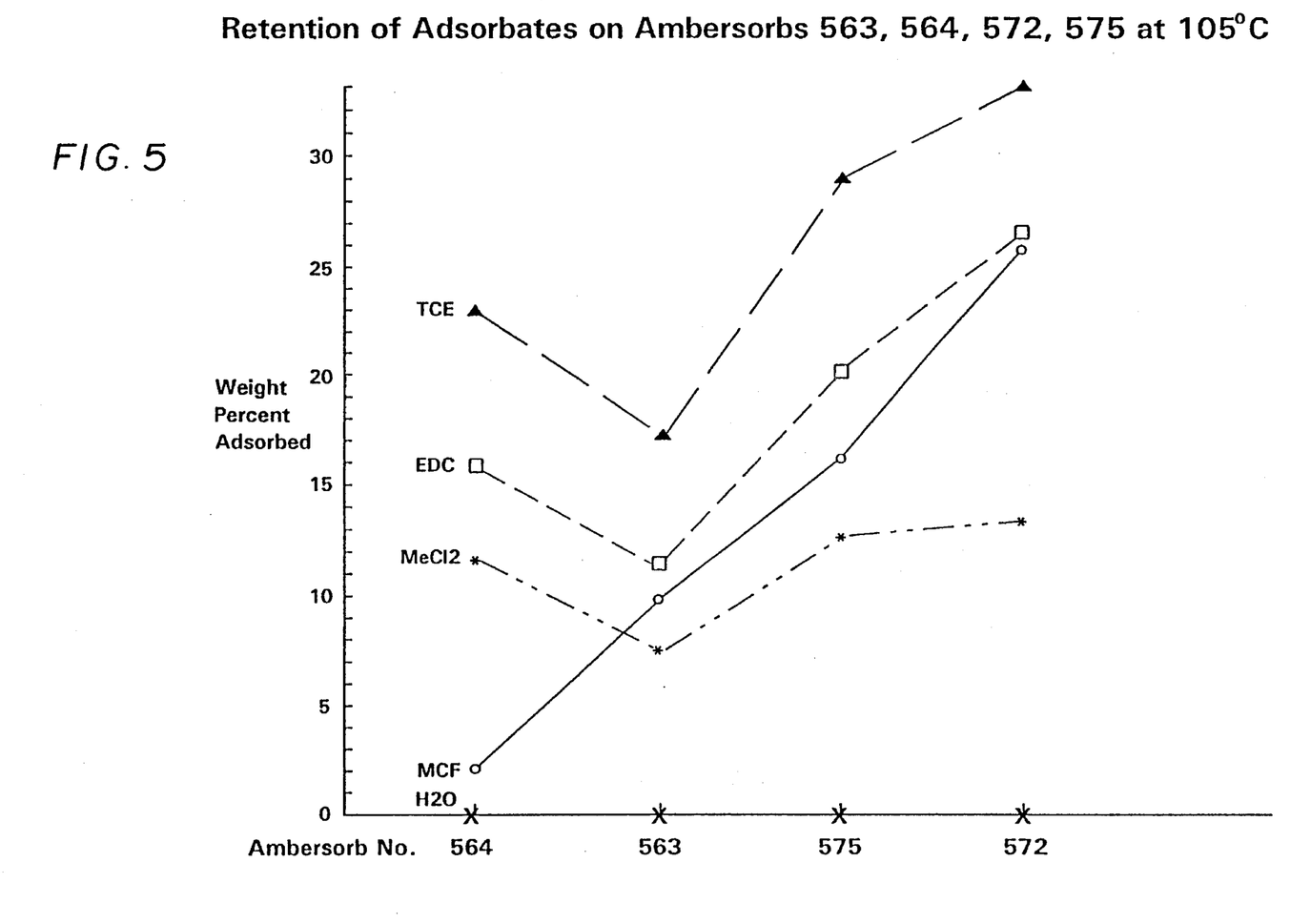
FIG. 5 is a composite, which shows adsorbate retention of 1,1,1-trichloroethane, dichloromethane, 1,2-dichloroethane and trichloroethylene at 105° C. plotted against four adsorbents.

The resulting thermal desorption curves are shown in FIGS. 1, 2, 3, and 4, where adsorbate retentions in weight percent are plotted against temperature. FIG. 5 is a composite, showing adsorbate retention at 105° C. plotted against the four "Ambersorb"™ adsorbents.

Example 5

Removal of Trichloroethylene and 1,2-Dichloroethane from "Ambersorb"™ 564 with Methylene Chloride Two 10 g samples of "Ambersorb"™ 564 were weighed out into two 125 ml screwcap bottles. To each was added 100 g of 1,1,1-trichloroethane containing 1000 ppm 1,2-dichloroethane (EDC) and 500 ppm trichloroethylene (TCE). Both bottles were placed on a shaker for two hours. At the end of that period as much of the solvent as could be removed with a suction pipet was removed from each bottle (close to 85 percent in each case). Analyses of the removed solvent samples showed no detectable 1,2-dichloroethane or trichloroethylene in each case (minimum detection limit=1 ppm).

The bottles were refilled to their original volumes with two low-boiling chlorinated extraction solvents, the first with methylene chloride and the second with 1,1-dichloroethane. The bottles were again subjected to the shaker for two hours. At the end of that period, samples of the extraction solvent were removed and analyzed for 1,2-dichloroethane and trichloroethylene, with the results shown below.

TABLE V

| Final Extraction Solvent | EDC Content, ppm | TCE Content, ppm |
|---|---|---|
| Methylene Chloride | 816 | 508 |
| 1,1-Dichloroethane | 610 | 275 |

Thus, methylene chloride extracted most of the 1,2-dichloroethane and essentially all of the trichloroethylene with an 85 percent volume replacement. This indicates that 1,2-dichloroethane and trichloroethylene can be quickly eluted from an adsorption column with methylene chloride as a liquid eluent if regeneration of the adsorbent is desired.

Example 6

Typical Bench-Scale Adsorption/Regeneration Cycle

Larger scale runs were made with "Ambersorb"™ 575 with equipment which allowed both the adsorption and steam regeneration cycles to be studied in the same apparatus, under conditions simulating plant operation. The physical characteristics of the adsorber bed are shown in Table VI.

The adsorption cycle was conducted in upflow configuration. Methylchloroform containing 484 ppm 1,2-dichloroethane (EDC) was pumped to the bottom of the adsorber bed from a constantly weighed vessel for control of feed rates. The bed effluent was analyzed continually with an online gas chromatograph (GC) to determine when 1,2-dichloroethane breakthrough of the bed occurred. Temperature measurements at the top and bottom of the bed were continuously recorded both during the adsorption step and during the regeneration steps. In some runs the bed was regenerated right after breakthrough occurred. In other runs regeneration was not started until the bed was saturated with 1,2-dichloroethane as determined from the online gas chromatograph.

The unit was then regenerated by thermal swing desorption. The adsorption column was insulated to conserve heat in the steam regeneration step. Valving allowed changeover from upward liquid flow during adsorption to downward gas/vapor flow during regeneration. The unit was configured so that either superheated steam or nitrogen could be used as the regenerating vapor. Once regeneration was complete, the bed was dried by purging with superheated nitrogen. When dry, the bed was cooled by purging with temperature had cooled to 100° F. (37.8° C.) or less, the adsorption process was repeated. Both the regeneration and cooling steps employed downflow. Table VI shows data obtained from a typical adsorption run. For this particular run adsorption was terminated and regeneration was begun upon breakthrough of 1,2-dichloroethane rather than upon total saturation of the bed.

TABLE VI

Bench Scale Adsorption Test

| Experiment No. | 6 |
|---|---|
| Adsorbent No. | 575 |
| Adsorbent Charge, g | 313.2 |
| Column Inside Diameter, cm | 2.731 |
| Column Length, cm | 91.4 |
| Material of Construction | Monel |
| Temperature at Top of Bed, °C. | 18.3 |
| Temperature at Bottom of Bed, °C. | 17.2 |
| Pressure at Top of Bed, psig | 0 |
| Pressure at Bottom of Bed, psig | 4 |
| Residence Time, minutes | 6.97 |
| Space Velocity, gallons/min./ft$^2$ | 3.206 |
| Methylchloroform Feed, ppm | |
| EDC | 484 |
| TC | 0 |
| cis-DCE | 12 |
| EDC Adsorbed at Breakthrough, g | 23.99 |
| EDC Loading Capacity, percent | 7.66 |

Example 7

Regeneration

A. Steam

A sample of approximately 5.00 g of "Ambersorb"™ 564 adsorbent weighed to four decimal places was placed in a tube such as described in Example 1B. The tube had an internal diameter above the sintered glass frit of 1.06 cm with a bed length of about 10 cm. Both ends were tapered down to fit ⅜-inch plastic tube fittings. The adsorbent was retained at the top with glass wool. The adsorbent was initially loaded to about 20 weight percent of its adsorbent capacity by contacting it with a mixture of 75 weight percent 1,2-dichloroethane and 25 weight percent trichloroethylene for a period of two hours and subsequently heating it overnight at 105° C. Shorter heating periods produced considerable variation in loading. The regeneration was carried out by producing steam from 80 ml of water preheated at from 180°–200° C. and passing the steam thus produced as the stripping agent at a uniform rate through the tube containing the preloaded "Ambersorb"™ adsorbent at a temperature of 180°–200° C. The loading/regeneration cycle was carried out 10 times without noticeable loss of adsorption capacity. About 1.5–2.0 weight percent of the adsorbed compounds remained on the adsorbent after each regeneration.

B. Nitrogen and Carbon Dioxide

The same procedure was followed as in part A, except that nitrogen was substituted for the steam as the stripping agent. Only a very slow flow rate should be used with this gas to minimize the inert component in the effluent, if the effluent is to be treated by incineration. The gas flow was regulated to 4.5 millimoles per hour. Using nitrogen, in 19.5 hours 98.5 percent of the adsorbed compounds were removed from the adsorbent.

The same procedure was again followed using carbon dioxide as the regenerate. As with nitrogen, only a very slow flow rate should be used. In 20.3 hours, carbon dioxide removed 94 percent of the adsorbed solvent. Thus, at the same flow rates steam was not nearly as efficient as either nitrogen or carbon dioxide.

Example 1 and Tables I and II both illustrate the comparative effectiveness of the "Ambersorb"™ adsorbents and various other adsorbents in the process of the present invention. The particular superiority of the "Ambersorb"™ 564 adsorbent can be seen from Table III. Example 2 illustrates the capacity and behavior of "Ambersorb"™ 564 in actual column tests. Example 3 illustrates the degrees of removal of various chlorocarbons, including 1,1,1,-trichloroethane, from the "Ambersorb"™ adsorbents which had been saturated with the chlorocarbons.

More specifically, the unique behavior of the "Ambersorb"™ 564 adsorbent in readily releasing most of its 1,1,1-trichloroethane while retaining other compounds, especially 1,2-dichloroethane and trichloroethylene, is illustrated in FIGS. 1–5, as referenced in Example 4.

Example 5 shows a unique attribute of methylene chloride when used for regeneration. In the example, methylene chloride is shown to desorb most of the 1,2-dichloroethane and trichloroethylene adsorbed on the "Ambersorb"™ 564 adsorbent. Thus, methylene chloride can be used to extract the 1,2-dichloroethane and trichloroethylene from the "Ambersorb"™ 564 adsorbent in a regeneration process, with the remaining methylene chloride being subsequently removed using steam or other stripping gas. Such a process is preferred as methylene chloride is more easily removed using steam or other gas than are the 1,2-dichloroethane and trichloroethylene.

Example 6 illustrates the effectiveness of the "Ambersorb"™ adsorbents, in particular, "Ambersorb"™ 575, in larger scale runs, under conditions simulating plant operation. In this example, both adsorption and steam regeneration cycles were studied.

Finally, Example 7 evidences the regeneration of loaded "Ambersorb"™ 564 adsorbent with steam and with inert gases and heat.

It should be understood that where percentages or proportions of materials are referred to in this specification or claims they are to be understood as being expressed on a weight basis.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

All references cited herein are incorporated by reference in their entirety, as if individually incorporated by reference.

What is claimed is:

1. A process for the purification of 1,1,1-trichloroethane initially comprising at least one undesirable $C_1$–$C_3$ chlorocarbon in an undesirably elevated concentration of up to about 10,000 ppm, which process comprises feeding said impure 1,1,1-trichloroethane into an adsorption zone, contacting said impure 1,1,1-trichloroethane in said adsorption zone with a particulate adsorbent at a temperature between about 0° and about 50° C. for a time sufficient to reduce the undesirable chlorocarbon in the 1,1,1-trichloroethane to not exceed the lesser of not more than 90 percent of said undesirably elevated concentration and in any event to not more than 100 ppm of undesirable chlorocarbon, said adsorbent being a particulate product of controlled pyrolysis of a polysulfonated macroporous crosslinked vinylaromatic polymer having a surface area of at lest about 500 m$^2$/g a micropore pore volume of at least about 0.24 ml/g, a macropore pore volume of less than about 0.24 ml/g and a ratio of macropore to micropore pore volume of less than about 100 percent, and withdrawing purified 1,1,1-trichloroethane from said adsorption zone.

2. The process according to claim 1, wherein said adsorbent has a surface area of between about 500 and 1100 m$^2$/g, a micropore pore volume of between about 0.24 and about 0.41 ml/g, a macropore pore volume of between about 0.14 and about 0.23 ml/g, and a ratio of macropore to micropore pore volume of between about 50 and about 90 percent.

3. The process according to claim 2, wherein said adsorbent has a surface area of between about 500 and about 600 m$^2$/g, a micropore pore volume of about 0.24 ml/g, a macropore pore volume of about 0.14 ml/g, and a ratio of macropore to micropore pore volume of about 58 percent.

4. The process according to claim 2, wherein said adsorbent has a surface area of between about 750 and about 850 m$^2$/g, a micropore pore volume of about 0.32 ml/g, a macropore pore volume of about 0.20 ml/g, and a ratio of macropore to micropore pore volume of about 63% percent.

5. The process according to claim 1, wherein the undesirable $C_1$–$C_3$ chlorocarbon is a member selected from the group consisting of 1,2-dichloroethane, trichloroethylene, 1,1-dichloroethane, cis-1,2-dichloroethylene, and a mixture of at least two of said compounds.

6. The process according to claim 1, wherein the undesirable $C_1$–$C_3$ chlorocarbon is initially present in the 1,1,1-trichloroethane in a concentration between about 1 and about 10,000 ppm.

7. The process according to claim 5, wherein the 1,1,1-trichloroethane initially comprises 1,2-dichloroethane in a concentration no greater than about 10,000 ppm.

8. The process according to claim 7, wherein 1,2-dichloroethane is initially present in the 1,1,1-trichloroethane in a concentration between about 1 and about 10,000 ppm.

9. The process according to claim 5, wherein trichloroethylene is initially present in the 1,1,1-trichloroethane in a concentration no greater than about 10,000 ppm.

10. The process according to claim 9, wherein the trichloroethylene is initially present in the 1,1,1-trichloroethane in a concentration of between about 10 ppm and about 10,000 ppm.

11. The process according to claim 5, wherein the 1,1,1-trichloroethane is contaminated with up to about 10,000 ppm of cis-1,2-dichloroethylene.

12. The process according to claim 11, wherein the 1,1,1-trichloroethane is contaminated with between about 10 and about 10,000 ppm of cis-1,2-dichloroethylene.

13. The process according to claim 1, wherein the concentration of undesirable chlorocarbon is reduced to between about 1 and about 50 ppm.

14. The process according to claim 13, wherein the concentration of undesirable chlorocarbon is reduced to between about 1 and about 10 ppm.

15. The process according to claim 1, wherein the concentration of undesirable chlorocarbon is reduced to less than about 1 ppm.

16. The process according to claim 1, wherein the process further comprises regeneration of the adsorbed chlorocarbons from the particulate adsorbent.

17. The process according to claim 16, wherein the process further comprises regeneration of the adsorbent chlorocarbons from the particulate adsorbent by elution with an eluent selected from methylene chloride, methanol, acetone or hot methylchloroform.

18. The process according to claim 16, wherein the process further comprises regeneration of the adsorbed chlorocarbons from the particulate adsorbent by stripping with steam or by heating.

19. The process according to claim 16, wherein the process further comprises regeneration of the adsorbed chlorocarbons from the particulate adsorbent by stripping with an inert gas selected from nitrogen, carbon dioxide, argon, methane, ethane or a mixture of at least two of said gases.

20. A process for selectively purifying impure 1,1,1-trichloroethane that is initially contaminated with at least one undesirable $C_1$–$C_3$ chlorocarbon that is present therein in an amount of between about 1 and about 10,000 ppm, which process comprises feeding said impure 1,1,1-trichloroethane through a column containing a particulate adsorbent at a temperature between about 0° and about 50 C. for a time sufficient to reduce the concentration of said undesirable chlorocarbon in the 1,1,1-trichloroethane to not more than 80 percent of its initial value and in any event to not more than about 100 ppm of undesirable chlorocarbon, said adsorbent being a carbonaceous particulate product of controlled pyrolysis of a polysulfonated macroporous crosslinked vinylaromatic polymer having a surface area of at least about 500 m$^2$/g, a micropore pore volume of at least about 0.24 ml/g, a macropore pore volume of less than about 0.24 ml/g and a ratio of macropore to micropore pore volume of less than about 100 percent.

21. The process according to claim 20, wherein at least one $C_1$–$C_3$ chlorocarbon is selectively regenerated from the adsorbent.

22. The process according to claim 20, wherein the undesirable $C_1$–$C_3$ chlorocarbon is a member of the group consisting of 1,2-dichloroethane, trichloroethylene and a mixture of same.

* * * * *